United States Patent [19]

Bey et al.

[11] 4,330,559

[45] May 18, 1982

[54] METHOD OF TREATING BENIGN PROSTATIC HYPERTROPHY

[75] Inventors: Philippe Bey, Strasbourg; Michel Jung, Illkirch Groffenstaden, both of France

[73] Assignee: Merrell-Toraude et Cie, Strasbourg, France

[21] Appl. No.: 231,072

[22] Filed: Feb. 3, 1981

Related U.S. Application Data

[63] Continuation-in-part of Ser. No. 28,739, Apr. 10, 1979, abandoned, which is a continuation-in-part of Ser. No. 814,765, Jul. 11, 1977, abandoned.

[51] Int. Cl.³ .................. A61K 31/195; A61K 31/16; A61K 31/22; A61K 31/165
[52] U.S. Cl. .................................... 424/319; 424/311; 424/320; 424/324
[58] Field of Search ................ 424/319, 311, 320, 324

[56] References Cited

U.S. PATENT DOCUMENTS 2,662,915 12/1953 Lowtz ................................. 260/534

OTHER PUBLICATIONS

Rawdo, Science, vol. 185, pp. 320-324 (7-26-1974).
Jof Men. Chem., vol. 17, No. 4, pp. 447-451 (1944).
Jof Med. Chem., vol 218, No. 4, pp. 600-604, 1975.
Burger, Medical Chem., 3rd Ed. Part I, 1970, pp. 65, 71 & 72.

*Primary Examiner*—Jerome D. Goldberg
*Attorney, Agent, or Firm*—David E. Frankhouser; Raymond A. McDonald; William J. Stein

[57] ABSTRACT

There is described a method for treating benign prostatic hypertrophy comprising the administration of 2,5-di-amino-2-(mono-,di-, or trifluoromethyl)pentanoic acid or derivative thereof.

8 Claims, No Drawings

METHOD OF TREATING BENIGN PROSTATIC HYPERTROPHY

This application is a continuation-in-part of copending application Ser. No. 28,739, filed Apr. 10, 1979, now abandoned, which is a continuation-in-part of application Ser. No. 814,765 filed July 11, 1977, now abandoned.

Benign prostatic hypertrophy, which is a common disease in men over age 50, causes variable degrees of bladder obstruction. In its advanced stages, such obstruction may require for treatment catheter drainage or, more definitively, surgery. There is, therefore, a need in medicine for a chemotherapeutic method for treating benign prostatic hypertrophy. Such a method is provided by the present invention. The term "benign prostatic hypertrophy" means any enlargement of the prostate whether it is due to hyperplasia of the cellular component or an increase in acinus size as a result of excessive secretion of prostatic fluid.

The invention sought to be patented comprehends a method of treating benign prostatic hypertrophy in patients in need thereof, which comprises the administration to said patient of an effective amount of a compound of the formula:

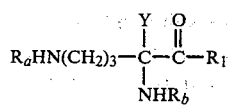

wherein:

$Y$ is $FCH_2-$, $F_2CH-$, or $F_3C-$;

$R_a$ and $R_b$ are, independently, hydrogen, $(C_1-C_4)$alkylcarbonyl, or the group

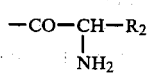

wherein $R_2$ is hydrogen, $(C_1-C_4)$alkyl, benzyl, or p-hydroxybenzyl;

$R_1$ is hydroxy, $(C_1-C_8)$alkoxy, the group $-NR_4R_5$, wherein $R_4$ and $R_5$ are, independently, hydrogen, or, $(C_1-C_4)$alkyl, or the group

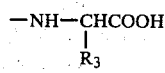

wherein $R_3$ is hydrogen, $(C_1-C_4)$ alkyl, p-hydroxybenzyl;

and the pharmaceutically acceptable salts and individual optical isomers thereof.

As used in Formula I, the term "$(C_1-C_4)$ alkylcarbonyl" means the group $-CO-$alkyl wherein the alkyl moiety has from 1 to 4 carbon atoms and is straight or branched, for example, methyl, ethyl, n-propyl, isopropyl, n-butyl, and isobutyl and tert-butyl. The term "$(C_1-C_4)$alky" means a straight or branched alkyl group having from 1 to 4 carbon atoms, such as methyl, ethyl, n-propyl, n-butyl, isopropyl and tert-butyl. The term "$(C_1-C_8)$ alkoxy" means an alkoxy group containing a straight or branched alkyl moiety having from 1 to 8 carbon atoms. Examples of $(C_1-C_8)$ alkoxy groups are methoxy, ethoxy, n-butoxy, n-pentyloxy, i-propoxy, and n-pentyloxy. Illustrative of acid addition salts of the compounds of the Formula I are the salts obtained with non-toxic organic or inorganic acids, such as hydrochloric, hydrobromic, sulfuric and phosphoric acids as well as acid metals salts such as sodium monohydrogen orthophosphate and potassium hydrogen sulfate. Illustrative organic acids which form suitable salts include mono, di and tricarboxylic acids, as for example, acetic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicylic, 2-phenoxybenzoic and sulfonic acids, such as methane sulfonic acid and 2-hydroxyethane sulfonic acid. Such salts can exist in either a hydrated or a substantially anhydrous form.

Also included are non-toxic salts formed with any suitable inorganic or organic bases. Illustratively, these salts include those of the alkali metals, as for example, sodium and potassium; alkaline earth metals, such as calcium and magnesium; light metals of Group III A including aluminium; and organic primary, secondary and tertiary amines, as for example, trialkylamines, including N,N'-dibenzylethylenediamine, dihydroabiethylamine, N-(lower)alkylpiperidine, and other amines which are known by those skilled in the art to form non-toxic salts. These salts are prepared by conventional means and can exist in either a hydrated or a substantially anhydrous form.

Preferred embodiments of the compounds of Formula I are those wherein $R_1$ is hydroxy. More preferred embodiments are the compounds of Formula I wherein $R_1$ is hydroxy and Y is $FCH_2-$ or $F_2CH-$. Still more preferred embodiments are the compounds of Formula I wherein either $R_a$ or $R_b$ is hydrogen, $R_1$ is hydroxy, and Y is $-CH_2F$ or $-CHF_2$.

Preferred compounds of Formula I are 2,5-diamino-2-difluoromethylpentanoic acid ("α-difluoromethylornithine" or "α-DFMO") and 2,5-diamino-2-fluoromethylpentanoic acid ("α-monofluoromethylornithine" or "α-MFMO").

It should be noted that the compounds of Formula I have an asymmetric center at the carbon atom which is alpha to the carboxyl group. Accordingly, the compounds may exist in either of their D- or L-configurations or as their DL-racemates. As used herein the compounds are intented to be used as their racemic mixtures or as individual enantiomers.

The compounds of Formula I produce in vivo irreversible inhibition of ornithine decarboxylase (ODC), the enzyme which catalyzes the decarboxylation of ornithine to putrescine. The decarboxylation of ornithine to putrescine is the first step in the biosynthesis of the polyamines-spermidine and spermine. Spermidine is formed by the transfer of an activated aminopropyl moiety from S-adenosyl S-methyl homocysteamine to putrescine, while spermine is formed by the transfer of a second aminopropyl group to spermidine. S-adenosyl S-methyl homocysteamine is formed by the decarboxylation of S-adenosylmethionine (SAM), a reaction catalyzed by the enzyme S-adenosylmethionine decarboxylase (SAM-DC).

The polyamines, which are found in all animal tissues and microorganisms, are known to play an important role in cell growth and proliferation. The induction of cell growth and proliferation is associated with both a marked increase in ODC activity and an increase in the levels of putrescine and the polyamines. Although the exact mechanism of the role of the polyamines in cell growth and proliferation is not known, it appears that the polyamines may facilitate macromolecular processes such as DNA, RNA, or protein synthesis. Polyamine levels are known to be high in the testes, ventral prostate, and thymus; in neoplastic tissue; in psoriatic skin lesions; and in other cells undergoing rapid growth processes.

Since putrescine is a precursor of the polyamines, it is seen that blockade of the conversion of ornithine to putrescine, such as by inhibition of ODC, can provide a method for regulating the cellular levels of the polyamines.

It is well known that benign prostatic hypertrophy is marked by an abnormal elevation of polyamine levels (see for example, *Cancer Research*, 38, 2321 (1978)). Hence, the polyamines may play an important role in the causation or maintenance of benign prostatic hypertrophy. It is believed that the compounds of Formula I may exert their therapeutic effect by blocking the formation of the polyamines and thereby interrupting or arresting the course of the enlargement of the prostate gland. It should be understood, however, that the process of this invention is not meant to be limited by any particular theory or mode of action.

The ability of the compounds of Formula I to irreversibly inhibit ornithine decarboxylase in vivo can be demonstrated as follows: An aqueous solution of the appropriate compound is given orally or parenterally to male mice or rats. The animals are sacrificed 1 to 48 hours after administration of the compound, and the ventral lobes of the prostate removed and homogenized. The activity of ornithine decarboxylase is measured as generally described by E. A. Pegg and H. G. Williams-Ashman, Biochem. J. 108, 533–539 (1968).

As pharmacologically useful agents, the compounds of Formula I can be administered in various manners to the patient being treated to achieve the desired effect. The compounds can be administered either alone or in combination with one another, or they can be administered in the form of pharmaceutical compositions, which are well known in the art. The compounds may be administered orally or parenterally (for example, intravenously, intraperitoneally, or subcutaneously), including injection of the active ingredient directly into the prostate. The amount of compound administered will vary over a wide range and can be any effective amount. Depending upon the patient to be treated, the severity of the condition being treated, the mode of administration, and the particular compound employed, the effective amount of compound administered will vary from about 10 mg/kg to 1 g/kg of body weight of the patient per day and preferably will be about 20 mg/kg to 150 g/kg of body weight of patient per day. For example, a typical unit dosage form may be a tablet containing from 100 to 500 mg of a compound of Formula I which may be administered to the patient being treated 1 to 10 times daily to achieve the desired effect. The term "effective amount," as applied to the treatment of benign prostatic hypertrophy, means the amount of compound administered which will significantly reduce the size of the prostate. The compounds can be administered from onset of hypertrophy of the prostate to regression of the symptoms.

As used herein the term patient is taken to mean warm blooded animals such as mammals, for example, dogs, rats and humans.

The solid unit dosage forms can be of the conventional type. Thus, the solid form can be a capsule which can be of the ordinary gelatin type containing a novel compound of this invention and a carrier, for example, lubricant and inert fillers, such as lactose, sucrose and corn starch. In another embodiment, the novel compounds are tableted with conventional tablet bases such as lactose, sucrose or corn starch in combination with binders such as acacia, corn starch or gelatin, disintegrating agents such as corn starch, potato starch, or alginic acid, and a lubricant such as stearic acid, or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The compounds of Formula I wherein $R_1$ is hydroxy and each of $R_a$ and $R_b$ is hydrogen are prepared by treating an ester derivative of ornithine, wherein the amino groups are suitably protected, with a strong base to form the carbanion intermediate which is reacted with a suitable halomethyl-halo alkylating reagent in an aprotic solvent, such as, dimethylsulfoxide, dimethylformamide, dimethylacetamide, benzene, toluene, ethers, such as, tetrahydrofuran, diethyl ether or dioxane and in the presence of hexamethylphosphortriamide, when Y is other than $F_2CH$—, at a temperature of about $-120°$ C. to $120°$ C., preferably about $25°$ to $50°$ C. for about ½ hour to 48 hours followed by acid or base hydrolysis as represented by the following reaction sequence.

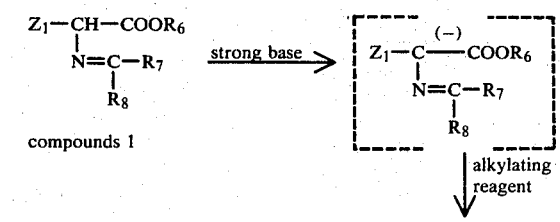

-continued

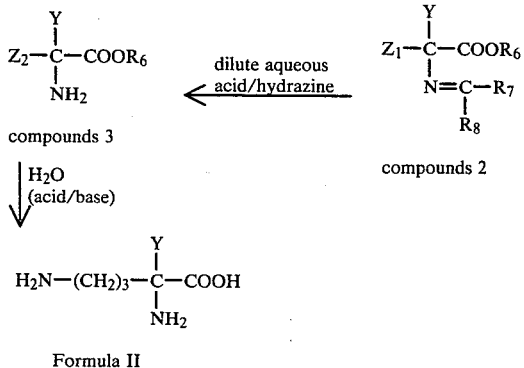

compounds 3 compounds 2

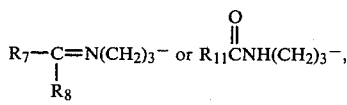

Formula II

In the above reaction sequence Y is $FCH_2-$, $F_2CH-$, or $F_3C-$; $R_6$ is $(C_1-C_4)$ alkyl (for example, methyl, ethyl, isopropyl, n-propyl or n-butyl); $R_7$ is hydrogen, phenyl, alkyl, methoxy or ethoxy; $R_8$ is phenyl or $(C_1-C_8)$ alkyl; or $R_7$ and $R_8$ taken together may form an alkylene group of from 5 to 7 carbon atoms, that is, $-CH_2-(CH_2)_m-CH_2-$ wherein m is an integer of from 3 to 5; $Z_1$ is

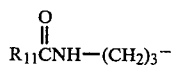

wherein $R_7$ and $R_8$ are the same and have the meanings defined above, and is phenyl, benzyl, or $C_1-C_4$ alkyl (for example, methyl, ethyl or isopropyl) and $Z_2$ is $H_2N(CH_2)_3-$ or $$R_{11}\overset{O}{\underset{\|}{C}}NH-(CH_2)_3{}^-$$

wherein $R_{11}$ has the above defined meanings. Illustrative examples of straight or branched $(C_1-C_8)$ alkyl groups which $R_7$ and $R_8$ may represent, are, for example, methyl, ethyl, n-propyl, isopropyl, n-butyl, tert-butyl, n-pentyl, neopentyl or triethylmethyl.

Suitable strong bases which may be employed in the above reaction sequence to form the carbanion intermediate are those which will abstract a proton from the carbon atom alpha to the carboxy group, such as an alkyl lithium, for example, butyl lithium or phenyl lithium; lithium di-alkylamides, for example, lithium diisopropylamide; lithium amide; sodium or potassium t-butylate; sodium amide; metal hydrides, for example, sodium hydride or potassium hydride; tertiary amines, such as, triethylamine; lithium acetylide; or dilithium acetylide. Lithium acetylide, dilithium acetylide, sodium hydride, lithium diisopropylamide, and tertiary sodium butylate are particularly preferred bases.

Suitable alkylating reagents which may be employed in the above reaction sequence are illustratively chlorofluoromethane, bromofluoromethane, fluoroiodomethane, chlorodifluoromethane, bromodifluoromethane, difluoroiodomethane, bromotrifluoromethane, chlorotrifluoromethane, and trifluoroiodomethane. When chlorodifluoromethane, bromodifluoromethane, and difluoroiodomethane are used for the alkylative reaction, rapid addition of the halomethyl halo reagent to the carbanion intermediate derived from the compounds of Formula I is necessary for optimal yields. The alkylating reagents are known in the art.

Removal of the protecting groups of the amine and carboxylic function may be achieved in one step by treatment of compounds 2 with aqueous acid, for example, hydrochloric acid or toluene sulfonic acid at a temperature of about 0° to 160° C. for about 4 to 24 hours to give compounds of Formula II. It is preferred to remove first the protecting groups of the amine function(s) of compounds 2 when said functions are protected as a Schiff's base by treating compounds 2 with dilute aqueous acid, for example, hydrochloric acid or with hydrazine or phenylhydrazine in solvents, such as, lower alcohols, for example, methanol or ethanol, ethers, chlorinated hydrocarbons, benzene and water. Removal of the protecting groups of the carboxylic functions and the amine groups when the amine groups are protected other than as a Schiff's base is achieved by treatment of compounds 3 with concentrated aqueous acids, for example, hydrobromic acid at a temperature of about 0° to 160° C. or in aqueous bases, for example, ammonium hydroxide.

The amine protected ester derivatives, that is, compounds 1, wherein $R_7$ is other than methoxy or ethoxy, are prepared by treating an appropriate amino acid ester with a carbonyl bearing compound to form a Schiff's base in a generally known manner, specifically: (a) when $R_7$ is hydrogen, by treating the appropriate amino acid ester with benzaldehyde or an alkanal having from 1 to 9 carbon atoms being straight or branched, for example, 1-propanol, 1-butanal, 2,2-dimethyl-propan-1-al or 2,2-diethylbutan-1-al; (b) when $R_7$ is phenyl by treating the appropriate amino acid ester with benzophenone or phenyl alkyl ketone wherein the alkyl moiety has from 1 to 8 carbon atoms and is straight or branched, for example, phenyl methyl ketone, phenyl ethyl ketone, phenyl isopropyl ketone, phenyl n-butyl ketone or phenyl tert-butyl ketone; and (c) when $R_7$ is a straight or branched alkyl group having from 1 to 8 carbon atoms, treating the appropriate amino acid ester with a phenyl alkyl ketone as described above or with a di-alkyl ketone wherein each alkyl moiety has from 1 to 8 carbon atoms and is straight or branched, for example, dimethyl ketone, diethyl ketone, methyl isopropyl ketone, di-n-butyl ketone or methyl tert-butyl ketone. The carbonyl bearing compounds are known in the art or may be prepared by procedures well known in the art.

When in compounds 1 $R_7$ is methoxy or ethoxy, an appropriate amino acid ester derivative is reacted with benzoyl halide, for example, chloride, or an alkanoic acid halide, for example, chloride, wherein the alkanoic acid has from 1 to 9 carbon atoms and may be straight or branched, such as, acetyl chloride, propionyl chloride, butyryl chloride, tert-butyryl chloride, 2,2-diethylbutyric acid chloride or valeryl chloride, at 0° C. in ethers, methylenechloride, dimethylformamide, dimethylacetamide or chlorobenzene in the presence of an organic base such as triethylamine or pyridine after which the reaction mixture is allowed to warm to about 25° C. for one hour. The resulting amide derivative is combined with an alkylating reagent, such as, methylfluorosulfonate, dimethylsulfate, methyliodide, methyl p-toluenesulfonate or trimethyloxonium hexafluorophosphate when $R_7$ is methoxy or triethyloxonium tetrafluoroborate when $R_7$ is ethoxy at about 25° C. in a chlorinated hydrocarbon solvent such as methylene chloride, chlorobenzene or chloroform, and the reaction mixture is refluxed for about 12 to 20 hours. The mixture is then cooled at about 25° C. and an organic base such as triethylamine or pyridine is added after which the solution is extracted with brine and the product isolated.

When in compounds 1 $R_7$ and $R_8$ together form an alkylene group of from 5 to 7 carbon atoms said amino acid ester derivatives are obtained by treating the amino acid ester with a cyclic alkanone selected from cyclopentanone, cyclohexanone and cycloheptanone to form a Schiff's base by procedures generally known in the art.

When in compounds 1,

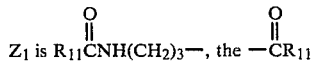

protecting group is added to ornithine by treatment of said amino acid with an excess of copper salt, for example, copper carbonate in boiling water for about 1 to 6 hours, and upon cooling to room temperature the insoluble materials are filtered off, and the filtrate is treated with an appropriate acid halide, for example, in acetone in the presence of a base such as sodium bicarbonate or sodium hydroxide followed by treatment with hydrogen sulfide. Illustrative acid halides which may be employed are acetyl chloride, propionyl chloride, benzoyl chloride or 2-phenylacetyl chloride.

The amino acid ester is formed by generally known procedures, for example, the amino acid is treated with an appropriate alcohol, such as, methanol, ethanol, or n-butanol saturated with HCl gas.

The compounds of Formula I wherein $R_a$ and $R_b$ are hydrogen, $R_1$ is hydroxy, and Y is —$CH_2F$ or —$CHF_2$ can be made by an alternative method, which is illustrated herein by Example 10 which describes the preparation of 2,5-diamino-2-fluoromethylpentanoic acid (α-monofluoromethyl ornithine or α-MFMO). α-DFMO can be prepared by an obvious modification of this process employing difluoroacetonitrile in place of fluoroacetonitrile.

Following is described the preparation of compounds of Formula I wherein $R_a$ and/or $R_b$ are other than hydrogen. The following description is applicable to all the above said compounds, however, it is necessary to protect one or the other of the amino groups prior to treatment with the appropriate reactant, that is, acid halide or anhydride, alkyl haloformate or acid of the formula

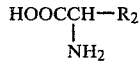

or anhydride thereof as described below to give compounds wherein either or both of $R_a$ and $R_b$ is other than hydrogen as follows: when $R_a$ is hydrogen and $R_b$ is other than hydrogen, the amino group to which $R_b$ is attached is protected as a copper salt by treatment of the corresponding derivative wherein $R_a$ and $R_b$ are hydrogen with an excess of a copper salt, for example, copper carbonate after which the amino group to which $R_a$ is attached is protected with, for example, benzyloxycarbonyl or tert-butoxycarbonyl by treatment with benzyl chloroformate or tert-butoxycarbonyl azide respectively followed by treatment with hydrogen sulfide, by procedures generally known in the art and illustrated more fully in the specific examples contained herein, prior to treatment with the appropriate reactant described below to give compounds wherein $R_b$ is other than hydrogen. The $R_a$ amine protecting group is subsequently removed by treatment with acid, for example, trifluoroacetic acid, HBr in dioxane or HBr in acetic acid or hydrogenolysis. The thus obtained compounds, that is, compounds wherein $R_a$ is hydrogen and $R_b$ is other than hydrogen may be treated with the appropriate reactants described below to give compounds wherein $R_a$ and $R_b$ are both other than hydrogen and may be the same or different. In preparing compounds wherein $R_a$ is other than hydrogen and $R_b$ is hydrogen the amino group to which $R_b$ is attached is protected as a copper salt by treatment of the corresponding derivative wherein each $R_a$ and $R_b$ is hydrogen with an excess of copper salt, for example, copper carbonate prior to treatment with the appropriate reactant described below followed by acid or base hydrolysis and subsequently treating with hydrogen sulfide.

The compounds of Formula I wherein $R_a$ or $R_b$ is alkylcarbonyl wherein the alkyl moiety is straight or branched and has from 1 to 4 carbon atoms are prepared by treating the corresponding derivatives wherein $R_a$ or $R_b$ is hydrogen or is suitably protected or as to compounds of Formula I, $R_a$ is other than hydrogen as described above and $R_1$ is hydroxy with an acid halide of the formula

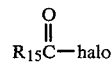

wherein halo is a halogen atom, for example, chlorine or bromine and $R_{15}$ is a straight or branched alkyl group having from 1 to 4 carbon atoms or an appropriate acid anhydride, in water in the presence of a base such as sodium hydroxide or sodium borate at a temperature of about 0° to 25° C. for about ½ hour to 6 hours. When appropriate, protecting groups are removed as described hereinabove by treatment with acid or hydrogenolysis.

The compounds of Formula I wherein $R_a$ or $R_b$ is

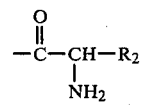

wherein $R_2$ is hydrogen, a straight or branched lower alkyl group of from 1 to 4 carbon atoms, benzyl or p-hydroxybenzyl and $R_1$ is hydroxy are prepared by treating the corresponding derivative wherein $R_a$ or $R_b$ is hydrogen or is suitably protected or as to compounds of Formula I, $R_b$ is other than hydrogen as described hereinabove with an acid of the formula

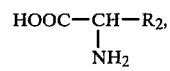

or an anhydride thereof, wherein the amino group is protected with a suitable blocking group such as benzyloxycarbonyl or tert-butoxycarbonyl and $R_2$ has the meaning defined hereinabove in an ether, such as, tetrahydrofuran or dioxane, methylene chloride or chloroform and in the presence of a dehydrating agent, such as, dicyclohexylcarbodiimide when the free acid is employed, at a temperature of about 0° to 35° C. for about 1 to 12 hours followed by acid and base hydrolysis and when appropriate, hydrogenolysis to remove the protecting groups.

The compounds of the Formula I wherein $R_1$ is a straight or branched alkoxy group of from 1 to 8 carbon atoms are prepared by converting the corresponding compounds wherein $R_1$ is hydroxy to the acid halide by, for example, treatment with thionyl chloride, followed by alcoholysis with an alcohol of the formula $R_{17}OH$ wherein $R_{17}$ is a straight or branched alkyl group having from 1 to 8 carbon atoms by procedures generally known in the art. Alternatively, compounds of Formula I wherein $R_1$ is a straight or branched alkoxy group of from 1 to 8 carbon atoms may be prepared from the corresponding derivative wherein $R_1$ is hydroxy by treatment of said derivative with an alcohol of the formula $R_{17}OH$ as defined above saturated with HCl for about 30 minutes for 12 hours at a temperature of about 25° C. to the boiling point of the alcohol.

The compounds of this invention wherein $R_1$ is $-NR_4R_5$ wherein each of $R_4$ and $R_5$ is hydrogen or a lower alkyl group of from 1 to 4 carbon atoms are prepared by an acylation reaction of an acid halide, for example, an acid chloride, of the corresponding compound wherein $R_1$ is hydroxy and $R_a$ and $R_b$ have the meanings defined in Formula I with the proviso that any free amino group is suitably protected with groups, such as, carbobenzyloxy or tert-butoxycarbonyl with an excess of an appropriate amine which may be represented as $HNR_4R_5$. The reaction is carried out in methylene chloride, chlroroform, dimethyl formamide, or ethers such as tetrahydrofuran and dioxane, or benzene at about 25° C. for about 1 to 4 hours. Suitable amines are ammonia, or a compound which is a potential source of ammonia, for example, hexamethylenetetramine; primary amines, for example, methylamine, ethylamine or n-propylamines; and secondary amines, for example, dimethylamine, diethylamine or di-n-butylamine. Following the acylation reaction the protecting groups are removed by treatment with acid, for example, trifluoroacetic acid or hydrogen bromide in dioxane.

The compounds of Formula I wherein

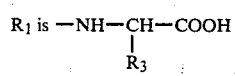

are prepared by reacting the corresponding derivative wherein $R_1$ is hydroxy or a functional derivative thereof, such as, an acid anhydride and $R_a$ and $R_b$ have the meanings defined in Formula I with the proviso that any free amino group is protected with a suitable blocking group, such as, benzyloxycarbonyl, tert-butoxycarbonyl by reacting the amine protected free acid with a compound of the structure

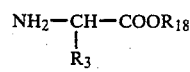

wherein $R_3$ has the meaning defined in Formula I and $R_{18}$ is a lower alkyl group, for example, methyl or ethyl in an ether solution, such as, tetrahydrofuran or dioxane at about 0° C. to 35° C. for about 1 to 20 hours followed by acid then base hydrolysis, for example, with 2 N aqueous $NH_3$ at about 0° to 50° C. for about 1 to 20 hours, to remove the protecting group(s), with the proviso that when the amine protected free acid is employed the reaction is carried out using a dehydrating agent such as dicyclohexylcarbodiimide.

The lactams of the compounds of Formula I wherein each of $R_a$ and $R_b$ is hydrogen and $R_1$ is hydroxy are prepared from the corresponding amino acid ester of the structure:

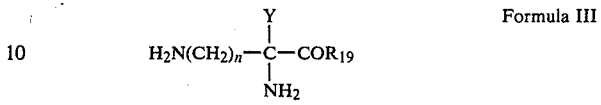

wherein n and Y have the meanings defined in Formula I, and $R_{19}$ is a straight or branched alkoxy group of from 1 to 8 carbon atoms, illustratively methoxy, ethoxy, isopropoxy, butoxy or hexyloxy, by treating said amino acid esters with an appropriate base, such as, sodium hydroxide, potassium hydroxide, lithium hydroxide, sodium carbonate, potassium carbonate, sodium methoxide, potassium methoxide, potassium tert-butoxide, sodium amide, or an organic amine such as a trialkylamine, for example, triethylamine in a solvent such as a lower alcohol, for example, methanol, ethanol, isopropyl alcohol, n-butanol, water, dimethylformamide, dimethylsulfoxide, hexamethylphosphortriamide or mixtures of these solvents for from ½ hour to 24 hours at a temperature of from about 0° to 120° C. optionally under a nitrogen atmosphere.

The compounds of Formula III are obtained by procedures generally known in the art from the corresponding amino acid, for example, by treating said amino acid with an appropriate alcohol, for example, methanol, ethanol, isopropyl alcohol, n-butanol or n-heptanol saturated with HCl gas.

The individual optical isomers of the compounds of Formula I wherein each of $R_a$ and $R_b$ is hydrogen and $R_1$ is hydroxy are obtained from the lactam of said compounds using a (+) or (−) binaphthylphosphoric acid salt by the method of R. Viterbo et al., Tetrahedron Letters, 48, 4617 (1971). Other resolving agents such as (+) camphor-10-sulfonic acid may also be employed. The individual optical isomers of compounds of Formula I wherein R is other than hydrogen and $R_1$ is other than hydroxy are obtained as described herein for the racemate only starting with the resolved free amino acid.

The following Examples illustrate the preparation of the compounds of Formula I, the preparation of certain pharmaceutical compositions suitable for oral administration, and the biological effect in rats obtained upon administration of an illustrative compound.

EXAMPLE 1

Dibenzaldimine Ornithine Methyl Ester

L-ornithine hydrochloride, 18 kg and 90 l of methanol are stirred at room temperature to obtain a reasonably uniform suspension. Hydrogen chloride gas is added to this suspension first passing into solution and then precipitating as the ester dihydrochloride. The introduction of hydrogen chloride is stopped and the reaction mixture is refluxed for one hour. Upon cooling to 5° C. for 3 hours, the ornithine methyl ester dihydrochloride is collected by filtration, washed with cold methanol, and vacuum dried at room temperature, yielding approximately 21.4 kg of material.

Approximately 6.8 kg of ornithine methyl ester dihydrochloride is suspended in 10 l of methylene chloride, cooled to 0° C. and 6.5 kg of benzaldehyde, dissolved in 10 l of methylene chloride, is added at such a rate as to maintain the reaction temperature at 0° to −5° C. The reaction mixture is allowed to warm to room temperature, stirring continued for an additional 2 hours, and 20 l of diethyl ether added thereto. Upon standing overnight, the triethylammonium hydrochloride that precipitates is removed by filtration, and the precipitate is washed with an additional 6.8 liters of diethyl ether. The combined filtrates are evaporated in vacuo and the residue dissolved in 34 l of diethyl ether. The organic solution is washed four times with 4 l of water, dried over anhydrous sodium sulfate, filtered and evaporated in vacuo to yield 9.28 kg of dibenzaldimine ornithine methyl ester as an oil.

EXAMPLE 2

2,5-Diamino-2-difluoromethylpentanoic acid (α-DFMO)

Tetrahydrofuran, 15 liters, are cooled to a temperature of −80° C. by the introduction of liquid nitrogen. Di-isopropylamine, 2.82 liters, is added under an atmosphere of nitrogen and twelve liters of a 15% solution of n-butyllithium, which is dissolved in hexane, is added to this mixture at such a rate as to maintain the temperature of the mixture at −75° to −80° C. To this mixture, still under nitrogen, is added 5.12 kg of dibenzaldimine ornithine methyl ester dissolved in 15 liters of tetrahydrofuran at such a rate that the reaction temperature remains between −75° and −80° C. The temperature of the reaction mixture is gradually increased to approximately 35° or 40° C. and maintained at that temperature under nitrogen for one hour. The nitrogen gas is replaced and approximately 13 kg of chlorodifluoromethane gas (Freon® 22) is added at such a rate as to maintain the reaction mixture at a temperature of 40° to 50° C. To this mixture is added 20 l of an aqueous saturated sodium chloride and 75 l of diisopropyl ether. The organic layer is separated and the aqueous layer extracted with 25 l of diisopropyl ether. The organic extracts are combined, washed four times with 20 l of aqueous saturated sodium chloride, dried over anhydrous sodium sulfate, filtered, and the filtrate evaporated in vacuo to an oil.

The oil residue is hydrolyzed with 30 l of 1 N-hydrochloric acid at room temperature for 3 hours, and reaction mixture is extracted three times with 5 l of chloroform. The combined aqueous layers are stirred for 15 hours at room temperature with 30 l of 10 N hydrochloric acid. The reaction mixture is extracted three times with 5 l of chloroform and the aqueous layer separated and evaporated in vacuo, diluted with 8 l of water and evaporated again in vacuo to remove the major portion of the acid present. The residue is diluted with 6 l of water and triethylamine added to a pH of 3.3. Charcoal, 100 g, is added to the mixture and the mixture warmed to 60°–70° C. for two hours. The mixture is filtered, washed with two liters of water and 80 l of acetone added to the filtrate. Upon standing overnight, the crude α-difluoromethylornithine which is obtained (2.1 kg) is filtered and washed with 2 liters of ethanol. Two recrystallizations of a portion of this crude material from a water-ethanol mixture yields 2,5-diamino-2-difluoromethylpentanoic acid, m.p. 183° C.

EXAMPLE 3

3-Amino-3-difluoromethyl-2-piperidone

To a solution of methyl-2-difluoromethyl-2,5-diamino-pentanoate-dihydrochloride (2.7 g) in dry methanol (30 ml) is added under nitrogen 2 equivalents of sodium methylate in methanol (0.46 g of sodium in 20 ml of methanol). The reaction mixture is stirred for 3 hours at room temperature then the solvent is evaporated under reduced pressure. The residue is extracted with ether to yield crude 3-amino-3-difluoromethyl-2-piperidone which is purified either by crystallization from CHCl$_3$/pentane: (mp: 149° C.) or by distillation (bp: 135° C./0.05 mmHg).

EXAMPLE 4

(−) and (+) 2-Amino-3-difluoromethyl-2-piperidone hydrochloride

To a solution of (−) binaphthylphosphoric acid (BNPA) (1.27 g) in hot ethanol (50 ml) is added a solution of (±) 3-amino-3-difluoromethyl-2-piperidone (0.546 mg) in hot ethanol (5 ml). On cooling, crystals separate. The reaction mixture is then let stand at 4° C. overnight. The precipitate is filtered off, washed with ethanol and diethyl ether to give 0.54 g of (−) binaphthylphosphoric salt ([α]$_D$= −409° C.=0.3, MeOH mp: 300° C.). Recrystallization of the mother liquor yields 0.15 g of (−) binaphthylphosphoric salt. Concentration of the filtrate gives 1.1 g of a sticky material which is treated with HCl 3 M at room temperature for 3 hours. The (−) BNPA is filtered off and the filtrate concentrated under reduced pressure. Recrystallization of the residue (320 mg) in ethanol affords (+) 3-amino-3-difluoromethyl-2-piperidonemonohydrochloride (160 mg) ([α]$_D$= +18°6, C=1, MeOh mp 238° C.). Treated in the same condition the (−) BNPA salt (436 mg) gives (−) 3-amino-3-difluoromethyl-2-piperidone monohydrochloride (137 mg) which is recrystallized in ethanol (67 mg) ([α]$_D$= −19°, C=1.02, MeOH; mp=240° C. dec.).

(−) and (+) 2-difluoromethyl-2,5-diamino pentanoic acid monohydrochloride (−) 3-Difluoromethyl-3-amino-2-piperidone hydrochloride (60 mg) is heated in HCl 6 M (4 ml) at reflux for 12 hours. After concentration under reduced pressure, the residue is dissolved in water and the pH of the solution is adjusted to 4.5 with a solution of NEt$_3$. The solution is then concentrated under reduced pressure and the residue extracted many times with chloroform and then recrystallized from H$_2$O/EtOH to give (+) 2-difluoromethyl-2,5-diamino pentanoic acid monohydrochloride (54 mg) ([α]$_D$= +6°, C=0.48; MeOH; mp≧240° C.). By an identical treatment, (+) 3-difluoromethyl-3-amino-2-piperidone hydrochloride (96 mg) gives (−) 2-difluoromethyl-2,5-diaminopentanoic acid monohydrochloride (56 mg) ([α]$_D$= −10°, C=0.7 MeOH, mp≧244°).

EXAMPLE 5

2,5-Diamino-2-difluoromethylpentanoic acid

Under nitrogen a solution (500 ml) of 2 M butyllithium in hexane is added to a stirred solution of 143.1 ml of diisopropylamine in 1.5 liters of tetrahydrofuran at −78° C. after which 261 g (0.81 mole) of ornithine dibenzylaldimine methyl ester in 1.5 l of tetrahydrofuran is added. Upon completion of the addition the reaction temperature is raised to 40° C. and maintained between 40° and 50° C. for 3 hours during which time chlorodifluoromethane gas is bubbled through the mixture with stirring. The reaction mixture is then treated with a saturated solution of sodium chloride. The organic material is extracted with ether, and the ether extract washed several times with sodium chloride solution, dried over magnesium sulfate and evaporated to give a viscous oil. The oil is stirred with 1 N HCl (1.5 l) for 3 hours, the mixture extracted several times with chloroform and the aqueous solution evaporated to dryness. The oily residue is refluxed with 12 N hydrochloric acid (1.5 l) for 16 hours, the cooled solution clarified by chloroform extraction before concentration, decolorization (charcoal), and further concentration to about 750 ml. The pH of the solution is adjusted to 3.5 by the addition of triethylamine, the solution treated again with charcoal before concentration to about 500 ml and dilution with 7–8 l of acetone. The precipitated product is filtered off and washed with ethanol. The crude product is recrystallized by dissolving in about 150 ml hot water and treatment of the solution with hot ethanol (450 ml). On cooling crystals of 2,5-diamino-2-di-fluoromethylpentanoic acid hydrochloride monohydrate separate; 71 g (37%), m.p. 183° C.

EXAMPLE 6

2-Amino-5-benzyloxycarbonylamino-2-difluoromethylpentanoic acid

To a solution of the copper salt of 2-difluoromethyl-2,5-diaminopentanoic acid in water, prepared by reacting 2-difluoromethyl-2,5-diaminopentanoic acid monohydrate hydrochloride (2.4 g) with copper carbonate (6 g), is added slowly at 0° C. with stirring 1.1 g of benzylchloroformate. The reaction mixture is stirred for an additional 3 hours at room temperature after which hydrogen sulfide is passed through the solution until it becomes colorless. The precipitate is filtered off, and the pH of the aqueous solution is adjusted to 6 by the addition of hydrochloric acid. Upon concentration 2-amino-5-benzyloxycarbonylamino-2-difluoromethylpentanoic acid is obtained.

By the above procedure only using tert-butoxycarbonylazide, acetylchloride or benzoylchloride in place of benzylchloroformate gives respectively 2-amino-5-tert-butoxycarbonylamino-2-difluoromethylpentanoic acid, 5-acetylamino-2-amino-2-difluoromethylpentanoic acid and 2-amino-5-benzyloxycarbonyl-2-difluoromethylpentanoic acid.

EXAMPLE 7

2-Acetylamino-5-amino-2-difluoromethylpentanoic acid

To a solution of 2.9 g of 2-amino-5-tert-butoxycarbonylamino-2-difluoromethylpentanoic acid in 10.5 ml of 1 M sodium hydroxide is added at 0° C. simultaneously 0.19 g of acetylchloride and 5 ml of 2 M aqueous sodium hydroxide. The reaction mixture is stirred for 3 hours at room temperature. The alkaline aqueous solution is then adjusted to a pH of 2 with hydrochloric acid and extracted with ethylacetate. After usual work-up the solvent is evaporated and the residue taken up in trifluoroacetic acid. After concentration and purification by ion exchange chromatography on a resin 5-amino-2-acetylamino-2-difluoromethylpentanoic acid is obtained.

EXAMPLE 8

5-Amino-2-difluoromethyl-2-(2-aminopropionylamino)-pentanoic acid

To a solution of 3.2 g of 2-amino-5-benzyloxycarbonylamino-2-difluoromethylpentanoic acid in 10 ml of 1 M aqueous sodium hydroxide is added at 0° C. simultaneously a solution of tert-butoxycarbonylazide, prepared from 3 g of tert-butoxycarbonylhydrazine, and a solution of 5.5 ml of 2 M aqueous sodium hydroxide. The reaction mixture is stirred overnight then extracted twice with 50 ml of ether. The alkaline aqueous solution is then adjusted to a pH of 2 with hydrochloric acid and extracted with ethylacetate. Usual work-up gives a solid residue which is dissolved in 15 ml of dry dimethylformamide and treated at room temperature with 1.6 g of benzylbromide in the presence of 2 ml of dicyclohexylamine. The reaction mixture is stirred for 14 hours and then the precipitate is filtered off. The filtrate is evaporated under reduced pressure. The resulting residue is partitioned between 100 ml of ethylacetate and water. The organic phase is washed successively with 20 ml of 1 normal aqueous hydrochloric acid, 20 ml of water, 20 ml of 5% aqueous sodium bicarbonate, 20 ml of water and 50 ml of brine then dried over magnesium sulfate. The solvent is evaporated and the residue taken up in 10 ml of trifluoroacetic acid. After 1 hour at room temperature the excess trifluoroacetic acid is stripped off under reduced pressure and the residue is taken up in a saturated solution of sodium bicarbonate and extracted with 50 ml of ether. The ether phase is dried over magnesium sulfate and then added at 0° C. to a solution of N-benzyloxycarbonyl-O-ethoxycarbonylalanine (2 g) in 20 ml of ether. Stirring is continued overnight at room temperature. The solvent is evaporated and the resulting syrupy residue is taken up in glacial acetic acid (20 ml) and hydrogenated over Pd/C 10% (200 mg). After completion of the hydrogen uptake the catalyst is filtered off. The filtrate is concentrated under reduced pressure with toluene and the residue purified by ion exchange chromatography on an acidic resin to give 5-amino-2-(2-aminopropionylamino)-2-difluoromethylpentanoic acid.

EXAMPLE 9

2-[(2,5-Diamino-2-difluoromethyl-1-oxopentane)amino]propionic acid

To a solution of 2,5-diamino-2-difluoromethylpentanoic acid monohydrate hydrochloride (2.35 g) in 10 ml of 2 M aqueous sodium hydroxide is added at 0° C. simultaneously a solution of 10 ml of 2 molar aqueous sodium hydroxide and a solution of tert-butoxycarbonylazide prepared from 3 g of tert-butoxycarbonylhydrazine. The reaction mixture is stirred overnight at room temperature and then extracted twice with 250 ml portions of ether. The alkaline aqueous solution is adjusted to a pH of 2 with hydrochloric acid and extracted with ethylacetate. After usual work-up the solvent is evaporated and the residue taken up in 40 ml of dry ether. After addition of 1 g of triethylamine an ether solution of 1 g of ethylchloroformate is added slowly at 0° C. with stirring. The precipitate is filtered off and the ether solution is added at once to a solution of alanine tert-butylester (1.5 g). Stirring is continued overnight and the solvent is evaporated. The residue is taken up in trifluoroacetic acid. After concentration and purification by ion exchange chromatography on an Amberlite 1R 120 resin 2-[(2,5-diamino-2-difluoromethyl-1-oxopentane)amino]-propionic acid is obtained.

EXAMPLE 10

2-Fluoromethyl-2,5-diaminopentanoic acid (α-MFMO)

A. 2-Fluoromethyl-2-amino-5-methoxy-valeronitrile

Under an atmosphere of nitrogen, 3-methoxypropyl magnesium chloride is prepared from 3-methoxy-1-chloropropane (5.43 g, 50 mmol, prepared according to Haworth and Perkin, Chem. Zentralblatt II 1271 (1912) and magnesium turnings (1.22 g, 50 mmol) in dry THF (50 ml). The mixture is heated under reflux for 3 hours, then cooled to $-30°$ C. and a solution of fluoroacetonitrile (2.95 g, 50 mmol) in THF (30 ml) is added during 20 minutes. After keeping the mixture at $-30°$ C. for $\frac{1}{2}$ hour more, a solution of sodium cyanide (4.9 g, 100 mmol) and ammonium chloride (8.09 g, 150 mmol) in water (100 mL), previously cooled to $0°$ C., is added and the mixture is stirred for $\frac{3}{4}$ hours at room temperature. After saturating with sodium chloride, the THF layer is separated and the aqueous phase is extracted twice with ether. After drying ($Na_2SO_4$), the combined organic extracts are evaporated to give 2-fluoromethyl-2-amino-5-methoxyvaleronitrile (4.0 g) as a brown oil.

NMR ($CDCl_3$) δ: 1.77 (4H, m), 2.10 (broad s, $NH_2$), 3.30 (3H, s), 3.40 (2H, t), 4.32 (2H, ABX, $J_{AB}=9$ Hz, $J_{AX}=J_{BX}=J_{H-F}=47$ Hz).

B. 2-Fluoromethyl-2-phtalimido-5-methoxy-valeronitrile

To a solution of 2-fluoromethyl-2-amino-5-methoxy-valeronitrile (1.62 g, 10 mmol) and triethylamine (2.02 g, 20 mmol) in methylene chloride (30 mL), cooled to $-20°$ C., is added phthaloyldichloride (2.03 g, 10 mmol) in methylene chloride (10 mL). The mixture is allowed to warm up to room temperature overnight. After washing with water, 1 N HCl, water again, and drying ($Na_2SO_4$), the solvent is removed under reduced pressure to give 2.4 g (83%) of crude material. This is purified by chromatography on silica (ethyl acetate/petroleum ether 3:7).

NMR ($CDCl_3$): δ2.15 (4H, m), 3.23 (3H, s), 3.40 (2H, t, J=6 Hz), 5.02 (2H, ABX, $J_{AB}=9$ Hz, $J_{AX}=J_{BX}=J_{H-F}=46$ Hz), 7.77 (4H, s).

C. 2-Fluoromethyl-2-phthalimido-5-iodo-valeronitrile

2-Fluoromethyl-2-phthalimido-5-methoxy-valeronitrile (1.20 g, 4.14 mmol), trimethylsilyl iodide (3.2 g, 16 mmol) and chloroform (15 mL) are heated to $60°$ C. under nitrogen for 48 hours. After removal of the solvent, the residue is dissolved in chloroform, washed with water, sodium thiosulfate solution and water again, dried and evaporated to give the crude product as an oil (1.2 g). This is purified by chromatography on silica (ethyl acetate/petroleum ether 1:3) to give pure 2-fluoromethyl-2-phthalimido-5-iodo-valeronitrile.

NMR ($CDCl_3$) δ: 2.0 (4H, m), 3.10 (2H, t), 4.90 (2H, ABX, $J_{AB}=9$ Hz, $J_{AX}=J_{BX}=J_{H-F}=46$ Hz), 7.70 (4H, s).

D. 2-Fluoromethyl-2,5-diphthalimido-valeronitrile

2-Fluoromethyl-2-phthalimido-5-iodo-valeronitrile (1.20 g, 3.11 mmol) and potassium phthalimide (0.75 g, 4 mmol) are heated in dimethylformamide (25 mL) to $80°$ C. for 2 hours. After standing overnight at room temperature, the DMF is removed by vacuum distillation and the residue is dissolved in chloroform and washed with 1 N KOH and water. After drying ($Na_2SO_4$), evaporation gives 2-fluoromethyl-2,5-diphthalimidovaleronitrile as a solid.

NMR ($CDCl_3$) δ: 2.17 (4H, m), 3.73 (2H, t), 4.93 (2H, ABX, $J_{AB}=9$ Hz, $J_{AX}=J_{BX}=J_{H-F}=46$ Hz), 7.73 (8H, broadened s).

E. 2,5-Diamino-2-fluoromethyl pentanoic acid

2-Fluoromethyl-2,5-diphthalimido valeronitrile (1.21 g, 3 mmol) is refluxed with conc. hydrochloric acid (20 mL) for 4 days. After standing at room temperature for several hours, phthalic acid is removed by filtration, the filtrate is dissolved in 2 N HCl (20 mL) and carefully extracted with ether (5×10 mL). After evaporation, the residue is dried carefully under vacuum (oil pump) overnight. It is dissolved in dry ethanol (7 mL) and, after filtration, propylene oxide (0.3 g, 5 mmol) in ethanol (1 mL) is added to precipitate the monohydrochloride. This is collected after standing overnight at room temperature and recrystallized from water/ethanol to give pure 2,5-diamino-2-fluoromethyl-pentanoic acid, monohydrochloride; m.p. $260°$ C. (dec), TLC (EtOH/$NH_4OH$ 80/20):0.18.

NMR ($D_2O$) δ: 1.93 (4H, m), 3.10 (2H, broad t), 4.83 (2H, ABX, $J_{AB}=10$ Hz, $J_{AX}=J_{BX}=J_{H-F}=46$ Hz).

EXAMPLE 11

An illustrative composition for hard gelatin capsules is as follows:

| | |
|---|---|
| (a) 2,5-diamino-2-difluoromethyl pentanoic acid | 200 mg |
| (b) talc | 5 mg |
| (c) lactose | 10 mg |

The formulation is prepared by passing the dry powders of (a) and (b) through a fine mesh screen and mixing them well. The powder is then filled into hard gelatin capsules at a net fill of 215 mg per capsules.

EXAMPLE 12

An illustrative composition for tablets is as follows:

| | |
|---|---|
| (a) 2,5-diamino-2-difluoromethylpentanoic acid | 200 mg |
| (b) starch | 43 mg |
| (c) lactose | 45 mg |
| (d) magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 290 mg each.

EXAMPLE 13

An illustrative composition for an injectable suspension is the following 1 ml ampul for an intramuscular injection.

| | Weight percent |
|---|---|
| (a) 2,5-diamino-2-difluoromethylpentanoic acid | 20 |
| (b) polyvinylpyrrolidone | 0.5 |
| (c) lecithin | 0.25 |
| (d) water for injection to make | 100.0 |

The materials (a)–(d) are mixed, homogenized, and filled into 1 ml ampuls which are sealed and autoclaved 20 minutes at 121° C. Each ampul contains 200 mg per ml of novel compound (a).

EXAMPLE 14

The effect of the compounds of Formula I on inhibiting enlargement of the prostate can be demonstrated by determining the ability of a compound to reverse the testosterone-induced regeneration of the ventral prostate in castrated rats. In this test, a group of 5 adult castrated Sprague-Dawley rats is given testosterone, 1 mg/rat s.c., in sesame oil every 24 hours on days 7 to 18 after castration, while a second group of rats is treated similarly with testosterone plus a 200 mg/kg dose of the test compound in saline given every six hours on days 6 to 18. A control group recieves the vehicle only (saline and sesame oil) on days 7 to 18. After 18 days, the prostates are removed and weighed.

In the control group of rats, there is a significant and pronounced loss in weight of ventral prostate following castration. In the animals receiving testosterone alone, the testosterone induces a gain in weight of the ventral prostate. Active test compounds produce a significant decrease in the weight gain induced by testosterone. For example, when tested in the above-described procedure, the administration of 2,5-diamino-2-difluoromethylpentanoic acid ($\alpha$-DFMO) to testosterone-treated castrated rats gave a 50% reduction in prostate weight, as compared with the results obtained in castrated rats treated with testosterone alone.

In the same experiment, putrescine, spermine, and spermidine levels in the ventral prostate were determined in each group of rats. In castrated animals receiving both $\alpha$-DFMO and testosterone, there was no formation of putrescine and spermidine while formation of spermidine was 50% less, as compared to the results obtained in animals receiving testosterone alone. Also, an histological examination of prostatic tissue of the above groups of animals showed at day 18 a 50% decrease in lumen or acinic diameter and a significant decrease in the volume of secretion present in the lumen.

What is claimed is:

1. A method of treating benign prostatic hypertrophy in a patient in need thereof which comprises the administration to said patient of an effective amount of a compound of the formula $$R_a HN(CH_2)_3 - \overset{\overset{Y}{|}}{\underset{\underset{NHR_b}{|}}{C}} - \overset{O}{\overset{\|}{C}} - R_1$$

wherein:
Y is $FCH_2-$, $F_2CH-$, or $F_3C-$;
$R_a$ and $R_b$ are, independently, hydrogen, ($C_1$-$C_4$)alkylcarbonyl, or the group $$-CO-\underset{\underset{NH_2}{|}}{CH}-R_2$$

wherein $R_2$ is hydrogen, ($C_1$-$C_4$) alkyl, benzyl, or p-hydroxybenzyl;
$R_1$ is hydroxy, ($C_1$-$C_8$)alkoxy, the group $-NR_4R_5$, wherein $R_4$ and $R_5$ are, independently, hydrogen, or, ($C_1$-$C_4$)alkyl, or the group $$-NH-\underset{\underset{R_3}{|}}{CHCOOH}$$

wherein $R_3$ is hydrogen, ($C_1$-$C_4$) alkyl, benzyl, or p-hydroxybenzyl;
or the pharmaceutically acceptable salts or individual optical isomers thereof.

2. A method as defined in claim 1 wherein Y is $-CH_2F$ or $-CHF_2$.

3. A method as defined in claim 1 or 2 wherein $R_1$ is hydroxy.

4. A method as defined in claim 1 or 2 wherein $R_1$ is hydroxy and $R_a$ is hydrogen.

5. A method as defined in claim 1 or 2 wherein $R_1$ is hydroxy and $R_b$ is hydrogen.

6. A method as defined in claim 1 or 2 wherein $R_a$ and $R_b$ are hydrogen.

7. A method as defined in claim 2 which comprises the administration of 2,5-diamino-2-fluoromethylpentanoic acid.

8. A method as defined in claim 2 which comprises the administration of 2,5-diamino-2-difluoromethylpentanoic acid.

* * * * *

UNITED STATES PATENT AND TRADEMARK OFFICE
CERTIFICATE OF CORRECTION

PATENT NO. : 4,330,559
DATED : May 18, 1982
INVENTOR(S) : Philippe Bey; Michel Jung It is certified that error appears in the above-identified patent and that said Letters Patent is hereby corrected as shown below:

At Column 2, Line 46 the patent reads: "intented" and should read --intended--.

At Column 6, Line 31 the patent reads: "1-propanol" and should read --1-propanal--.

At Column 9, Line 30 the patent reads: "chlroroform" and should read --chloroform--.

At Column 17, Line 15 the patent reads: "recieves" and should read --receives--.

Signed and Sealed this

Fourteenth Day of November, 1989

*Attest:*

JEFFREY M. SAMUELS

*Attesting Officer*     *Acting Commissioner of Patents and Trademarks*